April 6, 1954 R. H. TALLEY, JR Plant Pat. 1,267
AZALEA PLANT
Filed May 5, 1953
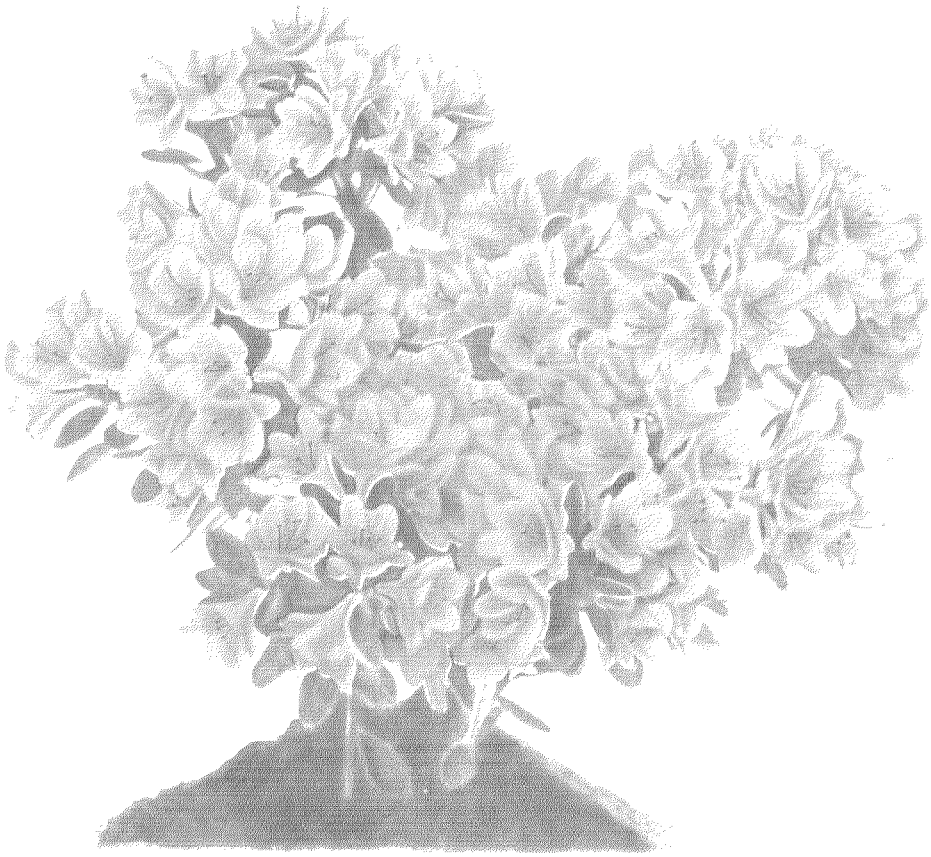
Inventor.
R. H. Talley, Jr.
By: Robb & Robb
attorneys.

Patented Apr. 6, 1954

Plant Pat. 1,267

UNITED STATES PATENT OFFICE 1,267

AZALEA PLANT

Robert H. Talley, Jr., Wachapreague, Va., assignor to Gulf Stream Nursery, Inc., Red Bank, N. J., a corporation of New Jersey Application May 5, 1953, Serial No. 353,250

1 Claim. (Cl. 47—60)

The present invention relates to a new and distinct variety of azalea plant which originated as a sport of the Azalea Kurume variety known as "Coral Bell" (unpatented). The new sport was discovered by me while digging plants for filling orders, in the nurseries of my assignee, at Wachapreague, Virginia.

At the time I discovered this new sport among cultivated plants of "Coral Bell," my attention was attracted to one plant in a nursery row which was substantially identical in all respects to the variety "Coral Bell," but which had blooms that were entirely different in color, whereupon, I examined the plant carefully and found that the "Coral Bell" parent plant had sported. Thereafter, I carefully preserved the sport and promptly took steps to asexually reproduce the same in order to develop it and ascertain whether the new color characteristic of the bloom was permanently established and transmissible by asexual reproduction.

In the course of asexually reproducing the new variety by cuttings at Wachapreague, Virginia, I found that the new variety did remain substantially identical to its parent "Coral Bell," except for the color of the flowers, while the new flower color also remained fixed and corresponds to that of the original sport which had a general color tonality of Salmon color, as distinguished from the typical Coral Pink general color tonality of the parent variety "Coral Bell."

The Salmon color of the flowers of my new variety definitely distinguishes the same from its parent, as well as from all other varieties of which I am aware, and represents an important improvement in azalea varieties, particularly when the flower color of my new variety is combined with the characteristics of "Coral Bell" other than the color of the flowers.

The accompanying drawing shows a typical specimen plant of my new azalea variety, with the flowers and foliage in different stages of development and depicted in color as nearly true as it is reasonably possible to make the same in an illustration of this character.

The following is a detailed description of my new variety, with color terminology in accordance with Ridgway's Color Standards and Nomenclature, except where general color terms of ordinary dictionary significance are obvious:

Parentage: Sport of Azalea Kurume "Coral Bell."

Propagation: Holds its distinguishing characteristics through succeeding propagations by cuttings.

*Plant*

(Observations made from plants grown outdoors in a nursery at Wachapreague, Virginia.)

Form of plant: Dwarf; compact.

Growth habit: Medium; dwarf; compact.

Blooming habit: Very free.

Blooming season: (Outdoors)—April-May. Suitability for forcing—excellent.

Foliage:

*Size.*—Small.

*Quantity.*—Abundant.

*Color.*—Deep Dull Yellow Green, Plate XXXII, high-lighted with Chromium Green, Plate XXXII.

*Shape.*—Oval-pointed.

*Texture.*—Upper side—glossy; under side—smooth.

*Edge of margin.*—Shape—plain.

*Disease resistance.*—As good as parent variety, as determined from comparison with "Coral Bell" grown under comparable cultural conditions at Wachapreague, Virginia.

*Flower*

Bloom:

*Flowers borne.*—In clusters; on strong, medium length stems.

*Quantity of bloom.*—Abundant, both outdoors and in greenhouse.

*Continuity.*—One season; about 2 weeks. Permanence—yearly; blooms once a year.

*Petalage.*—Number of petals under normal conditions—10. Color—Eosine Pink, Plate I, blending into Geranium Pink, Plate I, and shaded with Rose Doree, Plate I. General color tonality—Salmon. Texture—firm. Shape—hose-in-hose.

Bud: Color—Jasper Red, Plate XIII, high-lighted with Rose Doree, Plate I.

*Reproductive organs*

Stamens: Color—Rose Doree, Plate I.

Pollen: Color—brownish.

I claim:

A new and distinct variety of azalea plant, substantially as herein shown and described, characterized particularly as to novelty by its general similarity to its parent Azalea Kurume "Coral Bell" (unpatented), but being distinguished therefrom by the Salmon general color tonality of its flowers.

No references cited.